US012728416B2

(12) United States Patent
Samproni

(10) Patent No.: US 12,728,416 B2
(45) Date of Patent: Sep. 8, 2026

(54) LIQUID SENSOR ASSEMBLY, APPARATUS, AND METHODS

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1204 days.

(21) Appl. No.: 17/310,243

(22) PCT Filed: Feb. 3, 2020

(86) PCT No.: PCT/US2020/016355
§ 371 (c)(1),
(2) Date: Jul. 27, 2021

(87) PCT Pub. No.: WO2020/163216
PCT Pub. Date: Aug. 13, 2020

(65) Prior Publication Data

US 2022/0193673 A1 Jun. 23, 2022

Related U.S. Application Data

(60) Provisional application No. 62/801,956, filed on Feb. 6, 2019.

(51) Int. Cl.
*B01L 3/00* (2006.01)
*G01N 33/487* (2006.01)

(52) U.S. Cl.
CPC ... *B01L 3/502738* (2013.01); *B01L 3/502715* (2013.01); *G01N 33/487* (2013.01);
(Continued)

(58) Field of Classification Search
CPC ....... B01L 2300/123; B01L 2300/0887; B01L 2300/0645; B01L 2200/022; B01L 3/502715; B01L 3/502738; G01N 33/487
(Continued)

(56) References Cited

U.S. PATENT DOCUMENTS 5,186,431 A 2/1993 Tamari
5,222,876 A 6/1993 Budde
(Continued)

FOREIGN PATENT DOCUMENTS

WO 2016007716 A1 1/2016
WO WO-2016189302 A1 * 12/2016 ......... G01N 35/1097
WO 2017019609 A1 2/2017

OTHER PUBLICATIONS

European Search Report and Written Opinion of European Application No. 20752340.8 dated Feb. 16, 2022.
(Continued)

*Primary Examiner* — Michael L Hobbs
*Assistant Examiner* — Lenora A Abel

(57) ABSTRACT

Disclosed is a sensor assembly 100 including a sensor body having a flow channel therein configured to receive a test liquid, such as a bio-liquid, one or more moveable walls defining one or more wall portions of the flow channel, the one or more moveable walls configured to be moveable, such as to a first position, a second position, or even an intermediate position, to change a volume of the flow channel 102, and one or more sensor elements positioned in the flow channel. Volume in the flow channel may be minimized for testing neonatal specimens. Liquid testing apparatus and methods of testing test liquids are provided, as are other aspects.

18 Claims, 6 Drawing Sheets

(52) U.S. Cl.
CPC . *B01L 2200/022* (2013.01); *B01L 2300/0645* (2013.01); *B01L 2300/0887* (2013.01); *B01L 2300/123* (2013.01); *B01L 2400/0478* (2013.01); *B01L 2400/0481* (2013.01)

(58) Field of Classification Search
USPC ........................................................ 435/288.5
See application file for complete search history.

(56) References Cited

U.S. PATENT DOCUMENTS 5,589,639 A 12/1996 D'Antonio et al.
6,576,194 B1 * 6/2003 Holl .................... B01F 25/4332 356/73
7,875,791 B2 1/2011 Leonov et al.
8,318,479 B2 * 11/2012 Domansky .......... B01L 3/50273 435/293.1
9,945,804 B2 4/2018 Samproni
2002/0107468 A1 8/2002 Chevallet et al.
2005/0223783 A1 10/2005 Spivak
2012/0016405 A1 1/2012 Hamilton et al.
2017/0182493 A1 * 6/2017 Perroud ................. G02B 21/34
2017/0203294 A1 7/2017 Samproni
2018/0136247 A1 * 5/2018 Boutelle .......... G01N 35/00693
2018/0217127 A1 8/2018 Samproni et al.
2018/0223354 A1 * 8/2018 Chang ............... B01L 3/502715
2018/0256137 A1 9/2018 Heikenfeld et al.

OTHER PUBLICATIONS

International Search Report and Written Opinion of International Application No. PCT/US2020/016355 dated May 7, 2020.

* cited by examiner

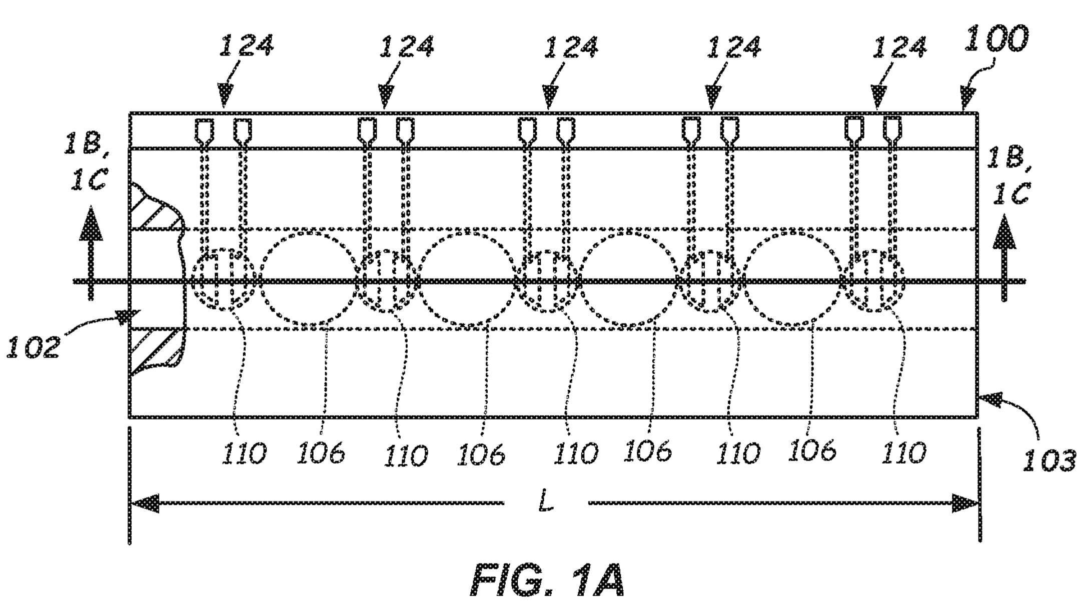
FIG. 1A
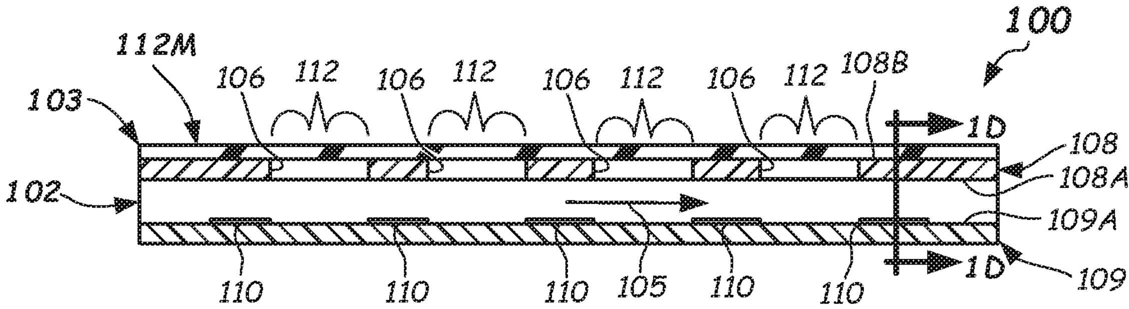
FIG. 1B
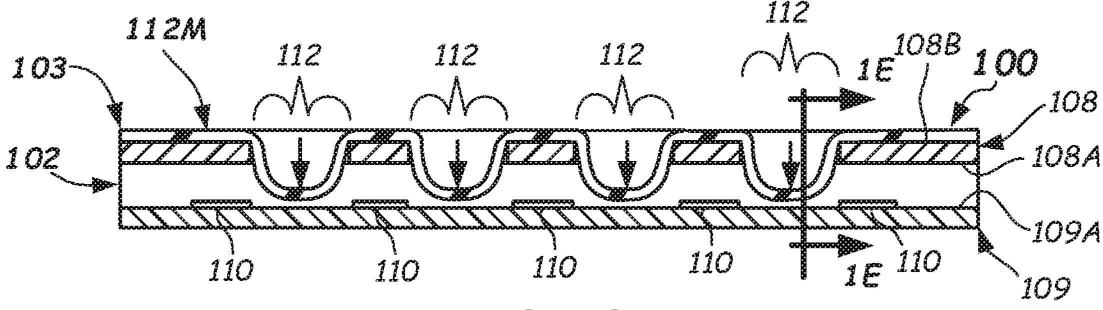
FIG. 1C
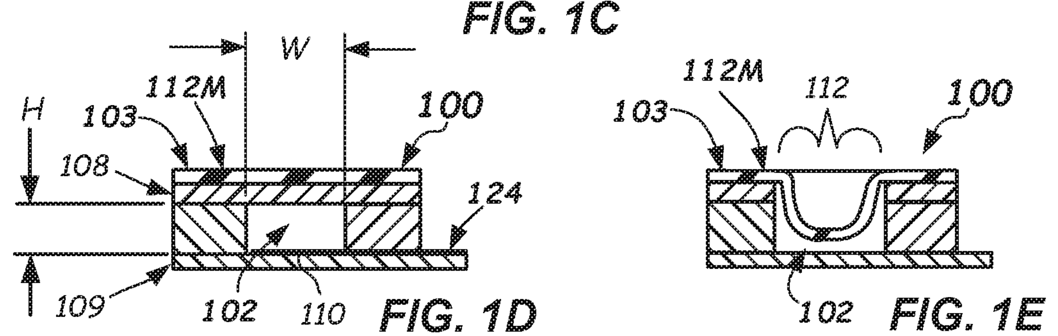
FIG. 1D
FIG. 1E 412
400
103
408
402
L
409
110
110
110
110
110
110
110

123
400
414
408
402
409
110
110
110
110
110
110
110
412

512
500
112M
506
508
112A
508A
502A
502B
502
509A
110
110
110
110
110
110
110
509
L 600
103
612
612
612
608
602
612M
606
612M
606
612M
606
110
110
110
110
110
110
110
110
110
609

LIQUID SENSOR ASSEMBLY, APPARATUS, AND METHODS

CROSS REFERENCE TO RELATED APPLICATIONS

This disclosure is a 371 of PCT/US2020/016355, filed Feb. 3, 2020, which claims benefit under 35 USC § 119 (e) of US Provisional Patent Application No. 62/801,956, filed Feb. 6, 2019, the disclosures of which are incorporated herein by reference in their entireties for all purposes.

FIELD

The present invention relates to test sensors and sensing methods, and particularly to test sensor assemblies configured to test for a presence of one or more constituents within a test liquid.

BACKGROUND

In liquid testing, such as in analyte testing of biological liquid specimens, a volume of a test liquid (e.g., blood or blood serum or plasma) can be provided in a pathway and sensors contained in the pathway can be used to sense certain identifiable constituents in the test liquid.

SUMMARY

Some embodiments of the present disclosure provide a sensor assembly configured to sense the presence of one or more constituents within a biological liquid (bio-liquid) specimen.

Some embodiments of the present disclosure provide a sensor assembly configured to measure an amount of one or more analytes contained in a specimen liquid obtained from a patient, wherein the available test liquid volume is very small, such as less than 100 μL, or even less than 50 μL in some embodiments.

Embodiments of the present disclosure provide a sensor assembly configured to minimize an amount of test liquid (e.g., specimen) used therein. The sensor assembly comprises a sensor body having a flow channel configured to receive a test liquid therein, one or more moveable walls defining wall portions of at least a part of the flow channel, the one or more moveable walls configured to be moveable to change a volume of the flow channel, and one or more sensor elements positioned in the flow channel at one or more locations where the one or more sensor elements can be contacted by the test liquid. In some embodiments, the volume of the flow channel can be reduced to enable testing of a small volume of test liquid (e.g., specimen), such as when obtained from a neonatal patient.

In a system aspect, a liquid testing apparatus is provided. The liquid testing apparatus comprises a sensor receiving chamber including at least an inlet channel coupled thereto; a sensor assembly received in the sensor receiving chamber, the sensor assembly further comprising: a sensor body having a flow channel configured to receive a test liquid from the inlet channel, one or more moveable walls defining wall portions of at least a part of the flow channel, the one or more moveable walls configured to be moveable to change (e.g., reduce) a volume of the flow channel, and one or more sensor elements positioned in the flow channel at one or more locations where the one or more sensor elements can be contacted by the test liquid.

According to another aspect of the present disclosure, a method of testing a test liquid is provided. The method comprises providing a sensor assembly comprising a sensor body having a flow channel therein, and one or more moveable walls defining wall portions of at least a part of flow channel, moving the one or more moveable walls to change a volume of the flow channel, and receiving a test liquid in the flow channel.

Still other aspects, features, and advantages of the present disclosure may be readily apparent from the following detailed description by illustrating a number of example embodiments and implementations. The present disclosure may also be capable of other and different embodiments, and its several details may be modified in various respects, all without departing from the scope of the present invention. Further features and aspects of embodiments will become more fully apparent from the following detailed description, the claims, and the accompanying drawings. Accordingly, the drawings and description are to be regarded as illustrative in nature, and not as restrictive. The invention is to cover all modifications, equivalents, and alternatives falling within the scope of the claims.

BRIEF DESCRIPTION OF THE DRAWINGS

The accompanying drawings, described below, are for illustrative purposes and are not necessarily drawn to scale. The drawings are not intended to limit the scope of the disclosure in any way. Like numerals are used throughout the specification and drawings to denote like elements.

FIG. 1A illustrates a top plan view of a sensor assembly according to one or more embodiments of the disclosure.

FIG. 1B illustrates a cross-sectioned side view of a sensor assembly taken along section line 1B-1B of FIG. 1A illustrating an example construction with moveable walls of a flow channel moved to a retracted position (e.g., a second position) according to one or more embodiments of the disclosure.

FIG. 1C illustrates a cross-sectioned side view of the sensor assembly taken along section line 1C-1C of FIG. 1A and illustrating an example construction with moveable walls of the flow channel moved to an extended position (e.g., a first position) according to one or more embodiments of the disclosure.

FIG. 1D illustrates a cross-sectioned end view of the sensor assembly of FIG. 1B and illustrating an example construction according to one or more embodiments of the disclosure.

FIG. 1E illustrates a cross-sectioned end view of the sensor assembly taken along section line 1E-1E of FIG. 1C illustrating moveable walls of the flow channel provided in a displaced (extended) condition according to one or more embodiments of the disclosure.

DETAILED DESCRIPTION

Figure 1F:
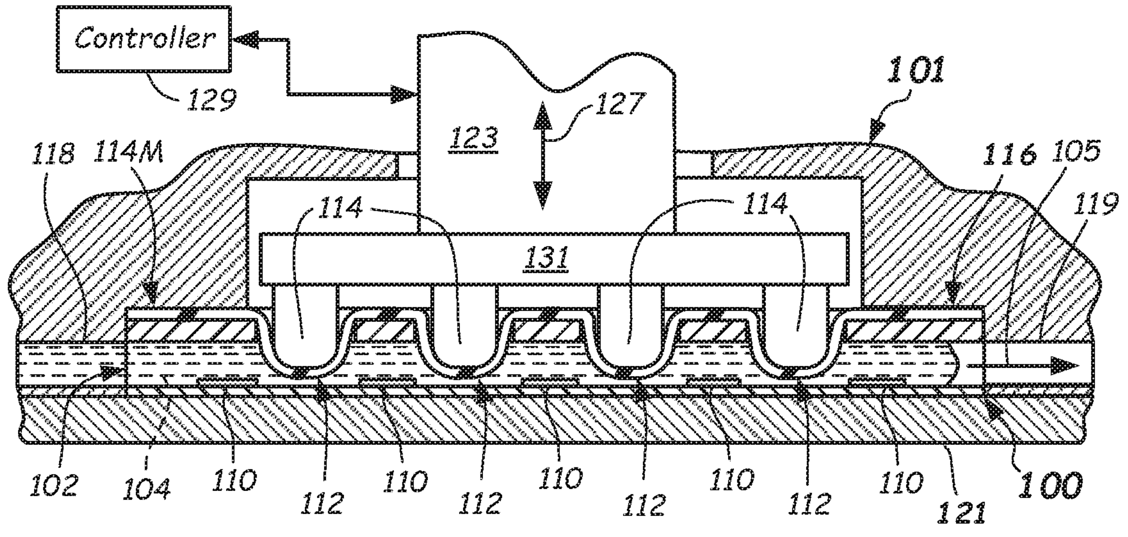
FIG. 1F illustrates a cross-sectioned side view of liquid testing apparatus that receives the sensor assembly of FIGS. 1A-1E wherein the moveable walls are displaced by deflectors to a displaced condition (e.g., flexed) according to one or more embodiments of the disclosure.
Figure 2:
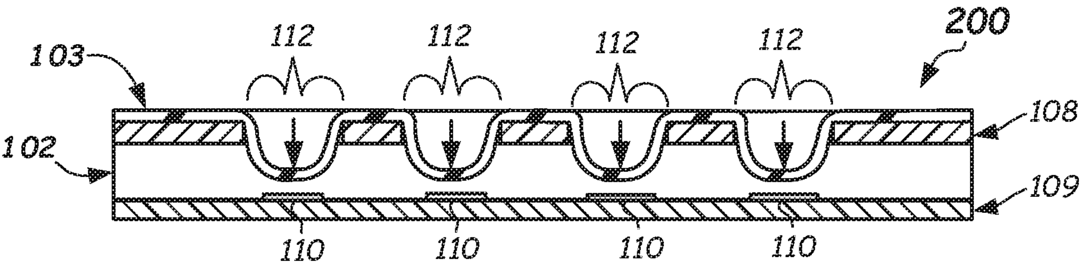
FIG. 2 illustrates a cross-sectioned side view of an alternative embodiment of sensor assembly illustrating sensor elements provided across the flow channel from the moveable walls (shown in a displaced condition) according to one or more embodiments of the disclosure.

In some tests, it may be desirable to test for more than one constituent in a test liquid (e.g., a specimen) at a time. For example, a sensor assembly that can test for twelve or more different constituents at a time is desirable. Moreover, in some instances the available volume of the test liquid (e.g., blood serum or plasma, or other bio-liquid) to be tested may be quite small, such as when taken from, for example, a neonatal patient. A neonatal patient as used herein means an infant of less than 28 days of age. In certain instances, it may be desirable to not only test for multiple constituents at one time in one sensor assembly, but the available volume of test liquid available for the tests may also be relatively small in volume, such as less than 100 μl or even less than 50 μl in some embodiments, for example.

Accordingly, in one aspect, an improved sensor assembly is provided that enables the carrying out of liquid testing (e.g., bio-liquid specimen testing) of multiple constituents simultaneously, while utilizing a relatively small volume of the test liquid, such as when the test liquid comes from a neonatal patient.

These and other aspects and features of the present disclosure will be described with reference to FIGS. 1A-10 herein.

In accordance with a first embodiment of the disclosure, as best shown in FIGS. 1A-1F, a sensor assembly 100 configured to enable liquid testing (e.g., bio-liquid testing) while using only a small volume of the test liquid is described. Although the present disclosure is generally focused on microfluidics and testing small volumes of test liquids (e.g., bio-liquids), the present disclosure is applicable to testing of other volumes of test liquids as well as testing for the presence of and/or concentration of multiple constituents in non-bio liquids. The sensor assembly 100 includes a sensor body 103 having a flow channel 102 formed therein. The flow channel 102 can be elongated having a length L extending along a length of the sensor assembly 100. The sensor body 103 may be made up of multiple pieces, for example. The flow channel 102 is configured to receive a test liquid 104 (FIG. 1F) therein, but may also be configured to receive other liquids therein, such as a wash liquid or a calibrator liquid, for example.

One or more moveable walls 112 are provided defining one or more wall portions of the flow channel 102. The one or more moveable walls 112 are configured to be moveable to change a volume of the flow channel 102 within the sensor assembly 100. Thus, under various conditions a selected volume capacity of the flow channel 102 may be selected. One or more sensor elements 110 are positioned in the flow channel 102. The one or more sensor elements 110 are positioned at one or more locations within the flow channel 102 where the one or more sensor elements 110 can be contacted by the test liquid 104 during testing. The one or more sensors elements 110 include a configuration enabling the testing of a concentration of a constituent contained in the test liquid. For example. Each of the one or more sensor elements 110 can include selectivity to a particular target chemical substance (e.g., an analyte) present in the test liquid (or calibrator liquid) in order to produce a measurable signal output that correlates to that particular concentration of that analyte in the test liquid 104. Thus, the one or more sensor elements 110 can comprise multiple analyte sensor elements, each capable of sensing a concentration of a particular analyte. For example, the one or more sensor elements 110 can comprise an array of analyte sensor elements that are arranged along a length L of the flow channel 104, such as at spaced distances along the length of the flow channel 102 extending in the flow direction 105 (see directional arrow in FIG. 1B). The dimensions of the length L, height H, and width W of the flow channel 102 can be as follows. The length L can be from 19 mm to 32 mm, the height H can be from 0.38 mm to 0.63 mm, and the width W can be from 0.56 mm to 0.94 mm, for example. Other suitable dimensions can be used.

The sensor assembly 100 can be configured to test for a concentration of a constituent in various types of the test liquid 104. For example, the test liquid 104 can be a bio-liquid selected from a group of whole blood, blood serum or plasma, urine, cerebrospinal (CSF) fluid, dialysate, serous fluid (such as pleural fluid, pericardial fluid, and peritoneal fluid), interstitial fluid, synovial fluid, intraocular fluid, lymph plasma, digestive fluid, and human tissue-containing liquid. Other bio-liquids and other types of liquids can be tested.

In more detail, the one or more moveable walls 112 are configured to be moveable from a first position to a second position, wherein the first position is at a different location transverse to the flow direction 105 than the first location. For example, in one embodiment, the one or more moveable walls 112 are configured to be moveable to and from a first position wherein the one or more moveable walls 112 are provided in an extended orientation as shown in FIG. 1C and a second position that is provided in an un-extended (e.g., retracted) orientation as shown in FIG. 1B. The terms extended and retracted are relative terms, meaning that the un-extended orientation may include some amount of extension, but less than in the extended orientation. In the extended orientation, the one or more moveable walls 112 may be fully flexed from the first fixed member 108 so that they contact the opposite wall of the second fixed member 109. Other degrees of extension wherein the one or more moveable walls 112 do not contact the opposite wall can be used.

Testing may take place while the one or more moveable walls 112 are located at the first position in some embodiments, such as when limited volume of the test liquid 104 is available. As shown, in some embodiments, the one or more moveable walls 112 comprise a portion that is flexible and is flexed when in the extended orientation. Contrarily, in a second position and in some embodiments, the one or more moveable walls 112 may be un-flexed in the un-extended orientation. In the second position, an operation such as a wash operation can be accomplished wherein a wash liquid is introduced into and may flow through the flow channel 102 to clean and remove and/or neutralize and residual test liquid 104. In some embodiments, the one or more moveable walls 112 may be provided in an intermediate position during testing (in between the first and second positions), as will be described further herein below.

To provide the mobility, the one or more moveable walls 112 can be made up from one or more flexible membranes 112M. As shown in FIG. 1B, the flexible membrane 112M may be a sheet of flexible material, such as a flexible polymer. The flexible membrane 112M may be bonded to or otherwise affixed to the first fixed member 108. For example, the flexible membrane 112M may be bonded to the first fixed member 108 with an adhesive, such as a pressure sensitive adhesive or the like. Flexible membrane 112M may have a thickness of from about 50 μm to 125 μm. Flexible membrane 112M may exhibit a hardness of from 10 to 100 on a Shore 00 durometer scale, for example. However, other suitable thicknesses and durometers may be used. The flexible membrane 112M, when provided as a flexible polymer, may comprise polyethylene perephthalate (PET), polyvinylpyrrolidone (PVP), thermoplastic elastomer (TPE), or ethylene propylene diene terpolymer (EPDM), and the like. Other suitable flexible materials and polymers may be used.

The first fixed member 108 may be a planar sheet of relatively rigid material (as compared to the flexible membrane 112M) and may have one or more channel side openings 106 formed therein. Four side channel openings 106 are shown. However, any number of channel side openings 106 may be provided, such as one, two, three, four, five, six or more channel side openings 106. The one or more flexible membranes 112M are configured to flex from the one or more channel side openings 106 and thus form the one or more moveable walls 112. The one or more moveable walls 112 are operably moveable (capable of movement, such as when conducting the test) to constrict a transverse cross-sectional area of the flow channel 102 as the one or more moveable walls 112 are moved from one transverse position to another. "Transverse" as used herein means perpendicular to the flow direction 105 as best shown in cross section in FIG. 1F.

As shown in FIGS. 1B and 1C, the one or more moveable walls 112 can be formed from one or more flexible membranes 112M that are bonded to a first fixed member 108 comprising the one or more channel side openings 106. The bonding configuration may be such that the one or more flexible membranes 112M are bonded to the first fixed member 108 on a second surface 108B thereof that is opposite from a first surface 108A defining a wall part of the flow channel 102 in the depicted embodiment.

Figures 4A, 4B, 5, 6:
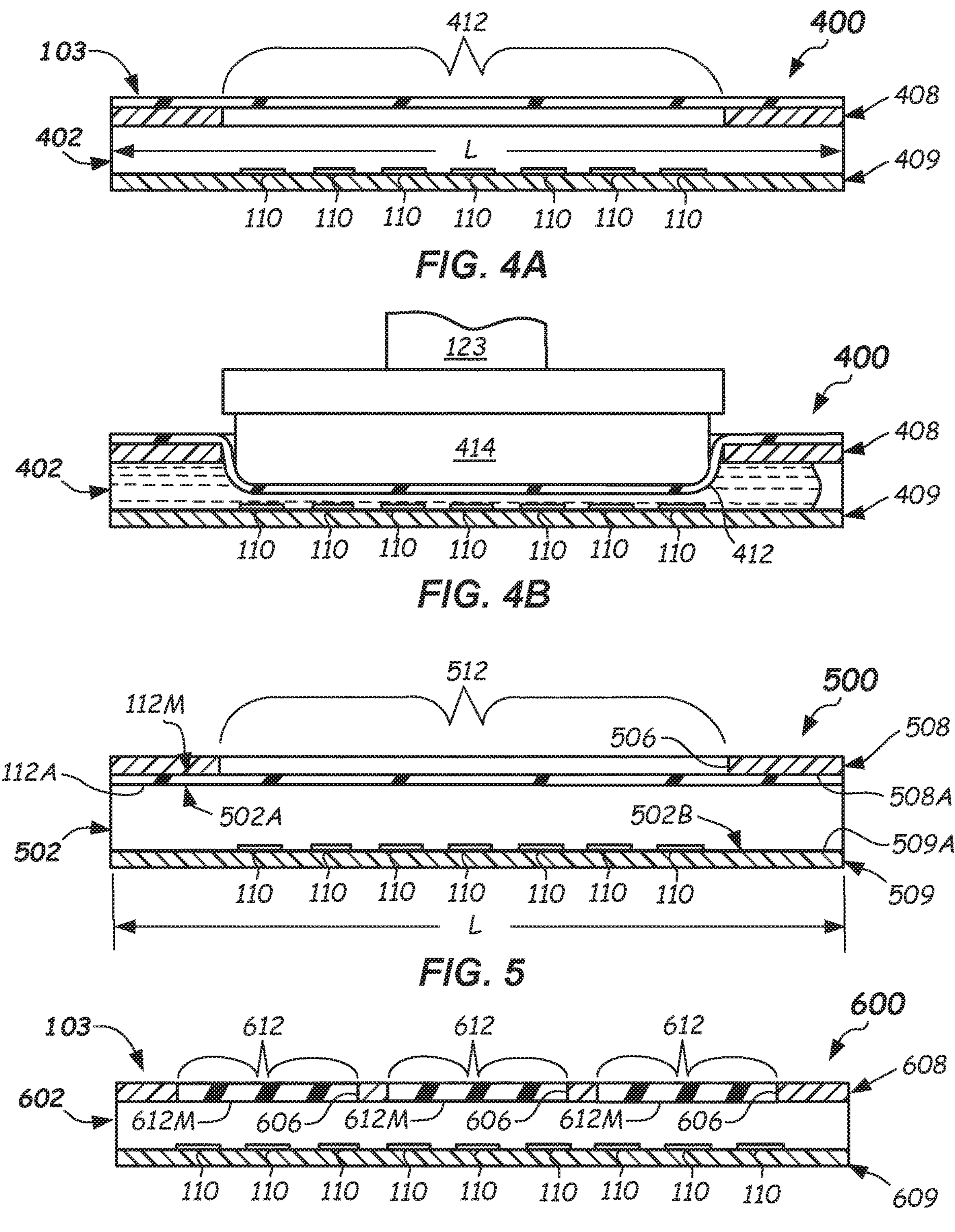
FIGS. 4A and 4B illustrate cross-sectioned side views of an alternative embodiment of sensor assembly comprising a single side opening and a single moveable wall shown in an un-displaced condition in FIG. 4A and shown in a displaced condition in FIG. 4B according to one or more embodiments of the disclosure.
FIG. 5 illustrates a cross-sectioned side view of another alternative embodiment of sensor assembly illustrating a flexible membrane comprising the moveable wall forming one side of the flow channel according to one or more embodiments of the disclosure.
FIG. 6 illustrates a cross-sectioned side view of another alternative embodiment of sensor assembly illustrating the one or more moveable walls formed in a side opening according to one or more embodiments of the disclosure.

In an alternative bonding configuration shown in FIG. 5, a moveable wall 512 is made up of a single flexible membrane 112M and a single channel side opening 506, wherein the single flexible membrane 112M is bonded to the first fixed member 508 on a first surface 508A thereof. In this alternative embodiment, a wall part of the flow channel 502 is formed by the exposed membrane surface 112A of the flexible membrane 112M. Thus, the one or more moveable walls 102 can comprise a membrane 112M bonded to a first fixed member 508 and forming one side wall 502A of the flow channel 502. Another wall part such as side wall 502B of the flow channel 502 can be defined by a second wall surface 509A of a second fixed member 509 positioned across the height of the flow channel 102. In the example embodiments of sensor assemblies 400, 500 of FIGS. 4A-5, the one or more moveable walls 412, 512 comprise a single moveable extending, for example, along 50% or more, 60% or more, 70% or more, or even 80% or more of a length L of the flow channel 402, 502 respectively.

In another alternative bonding configuration shown in FIG. 6, one or more moveable walls 612 are made from one or more flexible membranes 612M bonded to and extending between side walls of one or more channel side openings 606 formed in the first fixed member 608.

Figure 7:
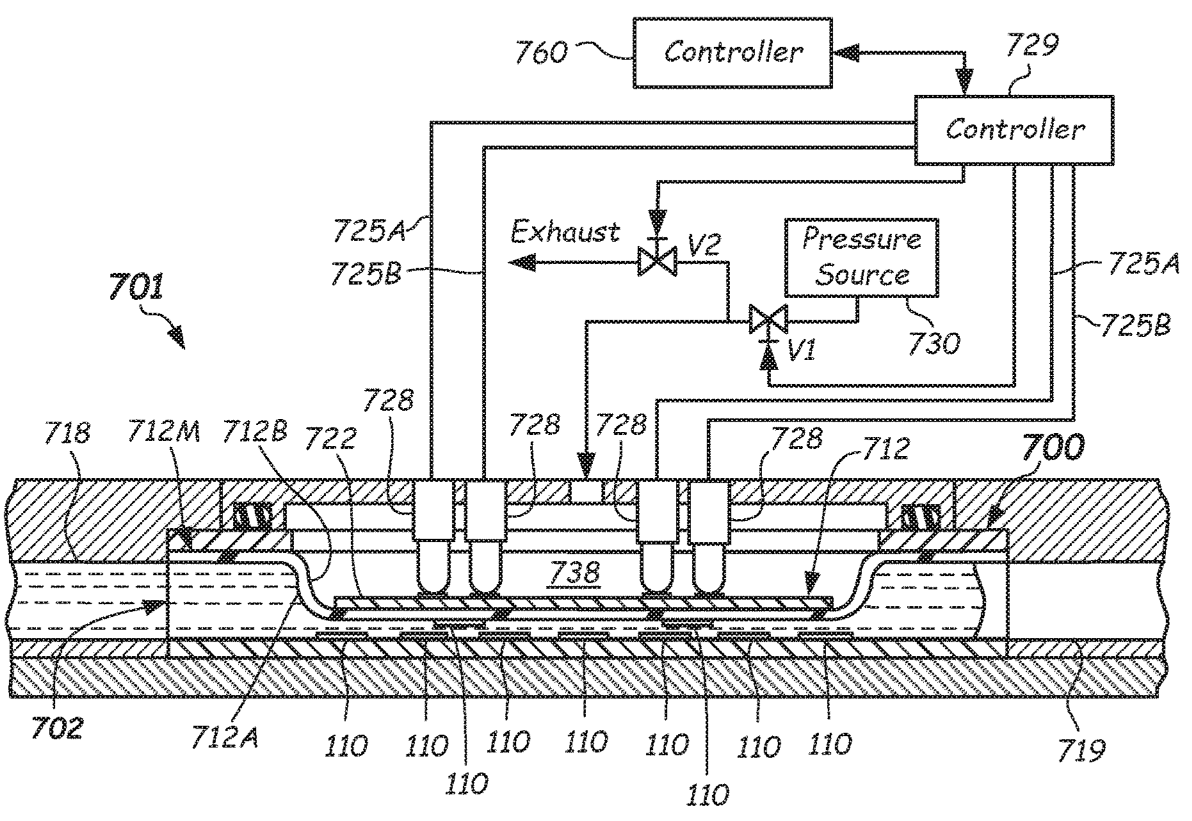
FIG. 7 illustrates a cross-sectioned side view of another alternative embodiment of sensor assembly illustrating the moveable wall being in a displaced condition by applying gas pressure to a backside of the moveable wall according to one or more embodiments of the disclosure.
Figure 8:
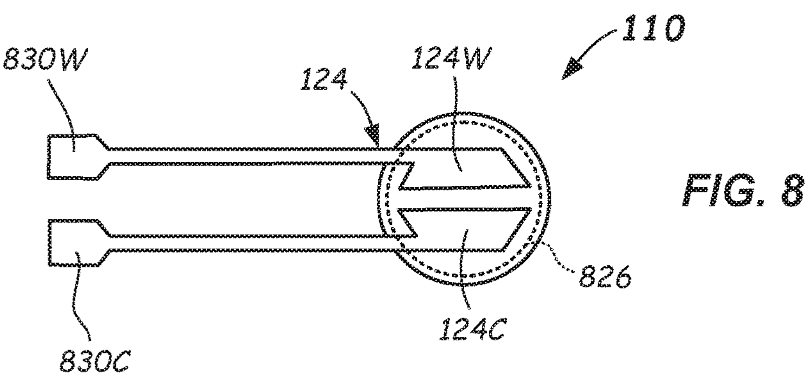
FIG. 8 illustrates a top view of an embodiment of sensor element illustrating one possible electrode layout according to one or more embodiments of the disclosure.

In an alternative embodiment shown in FIG. 7, a rigid member 722 may be further coupled to (e.g., bonded to) the flexible membrane 712M and thus form at least a portion of the moveable wall 712 that can move transversely over a relatively large area. Rigid member 722 may be coupled to an outside wall 712B of the flexible membrane 712M or optionally to the inside wall 712A. The rigid member 722 may be bonded into the flexible membrane 712M to provide a rigid central portion capable of purely transverse motion. The rigid member 722 is much stiffer (e.g., 5× or more) than the membrane 712M.

Various configurations and arrangements of the one or more sensor elements 110 can be provided. For each sensor element 110, there are provided electrodes 124 (FIGS. 1A, 1D), such as working electrode 124W and counter electrode 124C shown in FIG. 8. A reagent 826 (shown dotted) may be applied over the electrodes and is provided in direct contact with the test liquid 104 in the flow channel 102. Other portions of the electrodes 124 in the flow channel 102 can be masked so as to avoid contact with the test liquid 104. Electrodes 124 can include sensor leads 830W and 830C which are configured to be contacted by a contact mechanism (not shown) of a test liquid apparatus e.g., test liquid apparatus 101). Thus, sensor leads 830W and 830C provided at multiple pickup locations can be provided on the sensor assembly 100. The sensor leads 830W and 830C of each of the sensor elements 110 are electrically connected in use to a controller 129, which carries out the calculations and electronic communication to facilitate measurement of the various constituents in the test liquid 104.

Multiple configurations of the sensor elements 110 are possible. For example, in the example embodiment of FIG. 1A-1F the one or more sensor elements 110 can be provided on the second fixed member 109 located on an opposite side of the flow channel 102 from the one or more moveable walls 112. The one or more sensor elements 110 can be provided interspersed between the locations of the one or more moveable walls 112 or even outside of longitudinal locations of the one or more moveable walls 112 in the flow channel 102 as shown in FIG. 1A-1F.

Optionally, the one or more sensor elements 110 may be provided on the second fixed member 109, 409, 509, 609, 709 and located directly across from the one or more moveable walls 112, 412, 512, 612, 712 such as shown in FIGS. 4A-4B, 5, 6, and 7, respectively.

Figure 3:
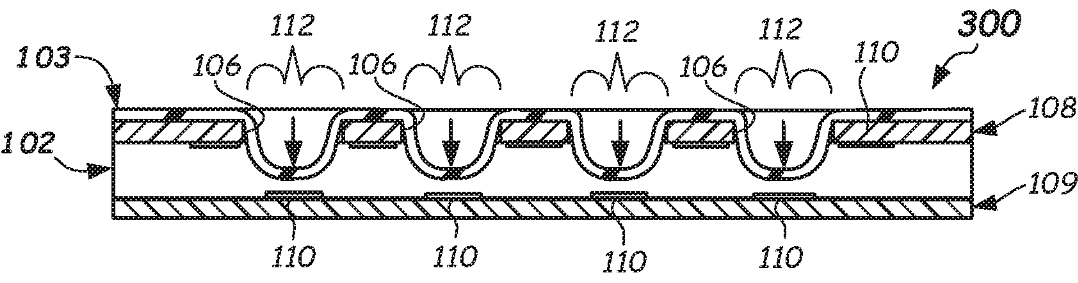
FIG. 3 illustrates a cross-sectioned side view of another alternative embodiment of sensor assembly illustrating sensor elements provided on two opposing sides the flow channel with the moveable walls shown in a displaced condition according to one or more embodiments of the disclosure.

As shown in the embodiment of FIG. 3, at least some of the one or more sensor elements 110 can be provided between channel side openings 106 formed in the first fixed member 108, and other ones of the one or more sensor elements 110 can be provided on either side of the channel side openings 106 on the first fixed member 108. Additionally, some of the one or more sensor elements 110 can be provided on the second fixed member 109, such as directly across from the one or more moveable walls 112, or otherwise positioned on the second fixed member 109.

As shown in FIG. 7, at least some of the one or more sensor elements 110 can be provided on the one or more moveable walls 712. When the one or more sensor elements 110 are provided on one or more of the moveable walls 712, then a connector mechanism for electrical communication with the one or more sensor elements 110, which are moveable with the one or more moveable walls 712 is provided. For example, as shown in FIG. 7, the communication from the one or more sensors 110 can be accomplished through one or more connector mechanisms 728 accommodating the motion, such as a pogo pin or other flexible electrical connector in electrical communication with communication lines 725A, 725B and electrical leads on the one or more sensor elements 110.

In FIG. 1F, in order to better understand its operation, the sensor assembly 100 is shown installed within a liquid testing apparatus 101, wherein a portion of the liquid testing apparatus 101 is shown. The liquid testing apparatus 101 comprises a sensor receiving chamber 116 including at least an inlet channel 118. The inlet channel 118 is configured to deliver the test liquid 104 to the sensor assembly 100. An outlet channel 119 may receive the test liquid 104 after the test and deliver it to a waste receptacle (not shown), for example. Flow of the test liquid 104 to the sensor assembly 100 may be provided by any suitable delivery mechanism, such as a pump, syringe, or other liquid movement method. Sensor assembly 100 is shown, but it should be understood, that sensor assemblies 200, 300, 400, 500, 600 could be substituted therewith with appropriate use of different numbers and sizes of deflectors (e.g., deflectors 114, 414).

One of the walls, such as wall 121, forming a part of the receiving chamber 116 may be detachable, pivotable, or otherwise movable, so as to allow insertion of the test assembly 100 into the receiving chamber 116. After insertion, wall 121 is repositioned as shown in FIG. 1F. Seals may be provided in the receiving chamber 116 at the interface of the flow channel 102 with the inlet channel 118 and outlet channel 119 to as to provide sealed interfaces at those locations. Any suitable seal may be used.

Once the sensor assembly 100 is received in the sensor receiving chamber 116, one or more deflectors 114, whose number is equal to the number of moveable walls 112, are moved into contact with the one or more flexible membranes 114M (one membrane shown). The one or more deflectors 114 are configured to contact and flex the one or more flexible membranes 114M and provide the mechanism for moving the moveable walls 112. The one or more deflectors 114 may be piston-like elements having a shape that can be matched with the shape of the channel side openings 106, but smaller so as to accommodate flexing of the one or more membranes 114M.

A motion producer 123 (only a portion shown), such as a linear actuator, solenoid, or other actuation device is coupled to (interconnected to) the one or more deflectors 114 to cause linear displacement thereof along the transverse direction shown by arrow 127. Motion is initiated by a control signal received from the controller 129. Deflectors 114 may be coupled to the motion producer 123 by a spanner member 131 allowing the defectors 114 to move in unison. Optionally, multiple motion producers (not shown) may be individually coupled to each of the multiple deflectors 114 and thus the moveable walls 112 may be individually actuated in any desired sequence. For example, in one sequence, the defectors 114 may be actuated from left to right to form a flow front moving the test liquid 104 from left to right in a flow direction 133, and to minimize any bubble capture.

In operation, the sensor assembly 100 further comprising the sensor body 103 containing the flow channel 102 receives the test liquid 104 from the inlet channel 118. The one or more moveable walls 112 defining one or more wall portions of the flow channel 102 are configured to be moveable to change a volume of the flow channel 102 at certain times during the testing. For example, depending on the available volume of the test liquid 104, the moveable walls 112 may be extended via action of the one or more motion producers 123 and the deflectors 114 to a first position (an extended position) as shown. In the first position shown, the volume of the flow channel 102 is minimized. For example, the moveable walls 112 may be actuated to the first position when commanded in response to a signal produced by the controller 129 responsive to a controller input, other input, or measurement indicating that the test liquid 104 is from a neonatal patient or that the volume of the test liquid 104 is less than a specified volume, such as less than 100 μl, for example.

The test liquid 104 may be introduced before or after the motion of the moveable walls 112 to the first position, but when the test liquid 104 is fully delivered, it is delivered to an extent in the flow channel 102 such that it is in intimate contact with all of the one or more sensor elements 110 positioned in the flow channel 102. Each of the sensor elements 110, as stated herein, may be directed to measuring a concentration of a certain target analyte, for example. Thus, the multiple different target concentrations can be tested at once.

Once the testing is completed to obtain suitable concentration measurements, the flow channel 102 can be washed by initiating a flow of a wash liquid (wash solution) from the inlet channel 118 through the flow channel 102. Flow may be provided by any suitable pumping mechanism (not shown) coupled to a supply of wash solution (e.g., soapy water or otherwise neutralizing liquid—not shown). When conducting the wash operation to wash out the test liquid 104, the moveable walls 112 may be moved (e.g., retracted) to a second position. The second position may be as shown, for example, in FIG. 1B wherein the one or more membranes 112M are in a less flexed condition, that may be un-flexed condition in some embodiments. Thus, in the second position, the cross-sectional area of the flow channel in the areas adjacent to the moveable walls 112 is larger than in the first position and thus allowing for larger flow volume, such as flow of the wash solution.

In another example of operation, the walls 112 may be actuated via the one or more motion producers 123 to an intermediate position between the first position and the second position wherein testing may be carried out. For example, the intermediate position may be used when the test liquid 104 is from an adult patient and thus there is sufficient volume for a more open channel configuration. The positioning to the intermediate position can be in response to a control signal from the controller 129 that the test specimen is from an adult patient or is otherwise above the threshold volume.

In some embodiments, the actuated position of the one or more moveable walls 112 may be responsive to a volume and/or mass of test liquid 104 that is available. Other intermediate positions may be utilized for other testing. For example, testing conducted utilizing a calibrator liquid may be carried out in the same intermediate position as when testing a test liquid from an adult.

As should be recognized, when sensor assemblies 400, 500 as shown in FIGS. 4A-4B and 5 are used, a single deflector 414 is used that is coupled to the motion producer 123. The motion producer can be the same as described above. Otherwise, these embodiments can be operated as discussed herein.

Referring now to FIG. 7, another embodiment of liquid testing apparatus 701 is shown. In this embodiment, the mechanism for actuating and moving the transverse position of the moveable wall 712 is gas pressure (e.g., air pressure) provided from a suitable pressure source 730 to an expansion chamber 738. Pressurizing the expansion chamber 738 with pressurized gas moves the position of the moveable wall 712. The extent of transverse motion of the moveable wall 712 is correlated to the chamber pressure. Thus, multiple positions of the moveable wall 712 can be achieved responsive to different amounts of applied pressure. Motion of the moveable wall 712 can be accommodated by pressurizing to a first set pressure to achieve extension motion to a first position, such as shown in FIG. 7, where the cross-sectional area of the flow channel 102 is reduced as compared to a retracted position. Pressurizing to the first set pressure can be achieved by closing valve V2 and opening valve V1 and applying a set pressure. A pressure regulator (not shown) may be provided if the pressure source is a canister of pressurized gas. Valve V1 can be a variable valve enabling pressurization of the expansion chamber 738 to any set pressure.

Optionally, the pressure source may be a pump, in which case the pump (not shown) would be operated until the set pressure is achieved, which could be monitored by measuring the pressure in the supply line or the expansion chamber 738 with a suitable pressure sensor. Deflation and retraction of the moveable wall 712 can be achieved by closing valve V1 and opening valve V2 such that the pressurized gas can be exhausted to the exhaust. In some embodiments, the controller 729 may be communicatively coupled to a laboratory information system (LIS) 760, for example, so that analyte concentrations from the testing can be promptly sent to the originator or elsewhere as commanded.

Figure 9:
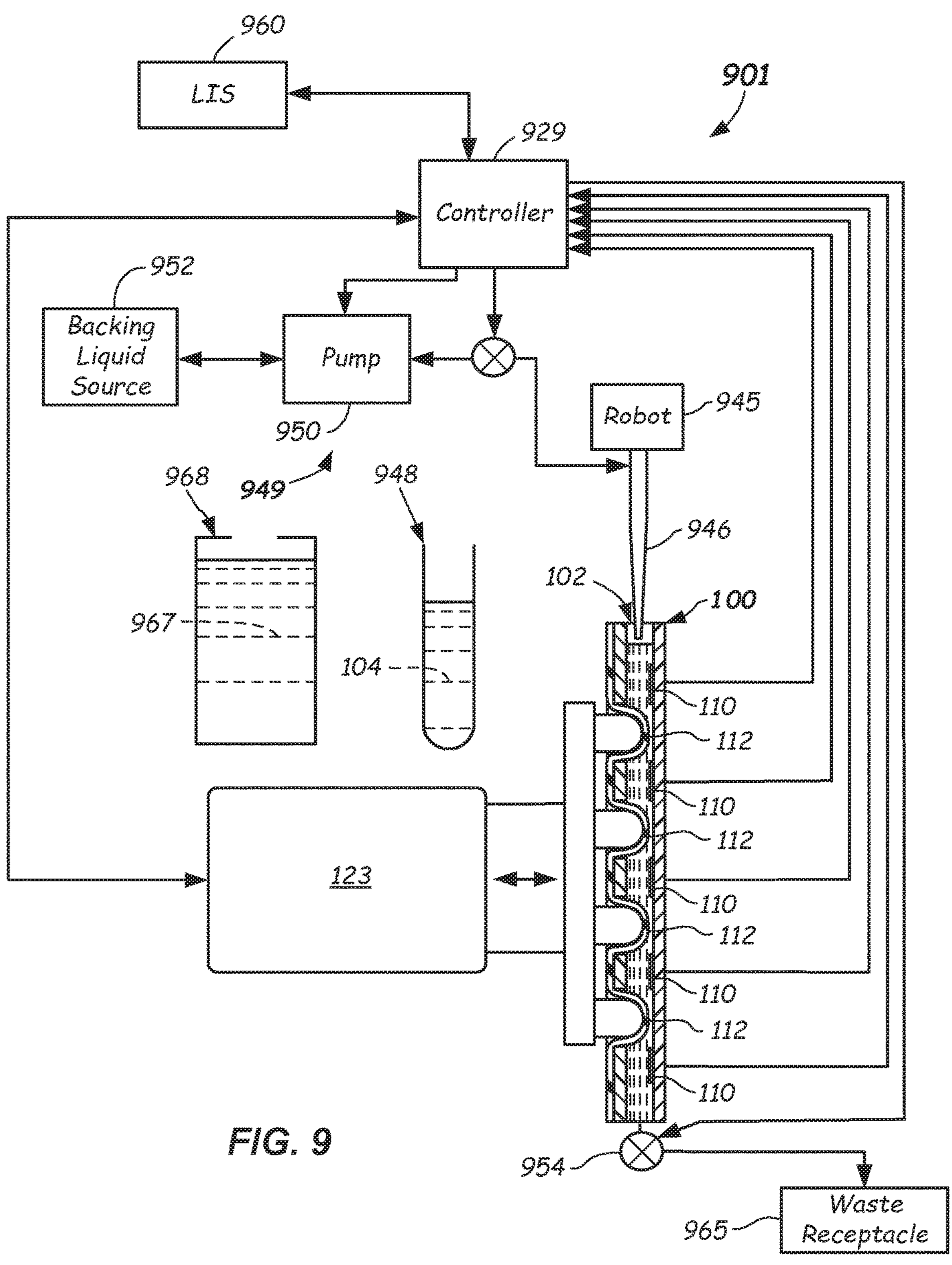
FIG. 9 illustrates a schematic side view of a liquid testing apparatus including an embodiment of sensor assembly including moveable walls according to one or more embodiments of the disclosure.

In FIG. 9, yet another embodiment of a liquid testing apparatus 901 utilizing a sensor assembly 100 including one or more moveable walls 112 is shown. In this embodiment, the mechanism for actuating and moving the position of the one or more moveable walls 112 can be an motion producer 123 or optionally gas pressure (e.g., air pressure) provided from a suitable pressure source like as shown in FIG. 7. The sensor assembly 100 used in this embodiment is positioned in an upright orientation as shown and can include any of the configurations of the sensor assemblies 100-700.

In operation, a robot 945 including a pipette 946 coupled thereto is moved via control signals from a controller 929 to a specimen container 948 including a test liquid 104 therein. Some, or all, of the test liquid 104 is aspirated by the pipette 946 via an aspiration system 949 fluidly coupled to the pipette 946. Aspiration can be carried out via action of a metering pump 950 pumping a backing liquid from a backing liquid source 852 (e.g., containing water) in the supply lines above the test liquid 104, as is conventional. Any suitable aspiration system 949 can be used.

The test liquid 104 is then dispensed from the pipette 946 into the flow channel 102, with base valve 954 closed. The moveable walls 112 can be moved by action of the motion producer 123 (e.g., linear actuator) to the desired position for the test. For example, when the amount of test liquid 104 is relatively small, such as when from a neonatal patient, the controller 929 can position the walls 112 at a first position (e.g., an extended position) wherein the volume of the flow channel 102 is minimized. In cases where the test liquid 104 is from an adult, the moveable walls 112 could be moved to a different position, such as an intermediate position.

The test can be run and the analyte measurements can be obtained from each sensor element 110 by communication with controller 929 and by way of conventional computations. Controller 929 may be communicatively coupled to a laboratory information system (LIS) 960, for example, so that analyte concentrations from the test can be promptly sent to the originator/requestor or elsewhere.

Following the test, the base valve 954 can be opened to flow the test liquid 104 to a waste receptacle 965. The flow channel 902 can then receive a wash solution 967 therein. Wash solution 967 can be aspirated into the pipette 946 by aspiration system 949 from a wash solution source 968, for example, and then dispensed with the base valve open or closed. With the base valve opened, the wash liquid can be dispensed along with robot motion to wash the sides of the flow channel 902. Multiple washes may be undertaken in some instances before commencing the next test to minimize carryover.

Figure 10:
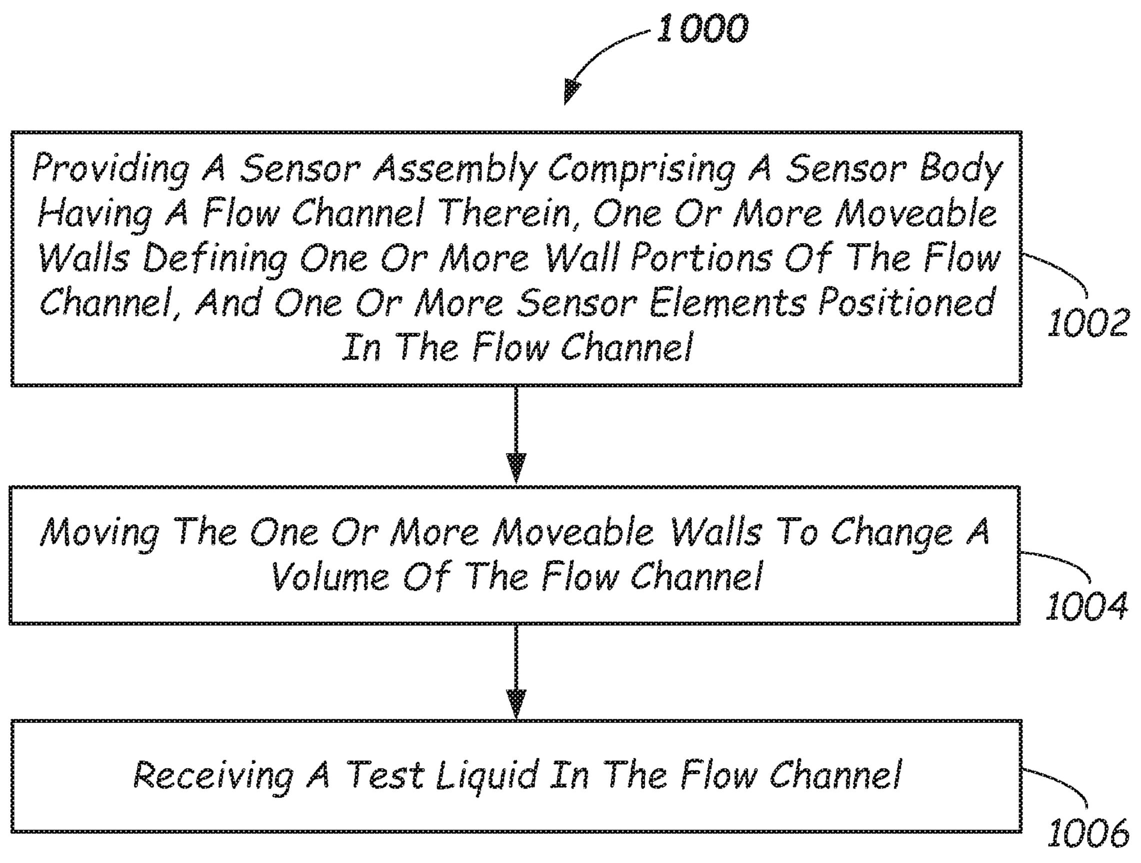
FIG. 10 illustrates a flowchart of a method of testing a test liquid according to embodiments.

According to another aspect, a method of testing a test liquid 104 according to embodiments will now be described with reference to FIG. 10. The method 1000 of testing a test liquid 104 includes, in 1002, providing a sensor assembly (e.g., sensor assembly 100, 100', 200, 300, 400, 500, 600, 700) comprising a sensor body (e.g., 103) having a flow channel (e.g., flow channel 102, 402, 502, 602, 702) therein, and one or more moveable walls (e.g., moveable walls 112, 412, 512, 612, 712) defining wall portions of at least a part of flow channel, and one or more sensor elements (e.g., sensor elements 110) positioned in the flow channel.

The method 1000 further includes, in 1004, moving the one or more moveable walls (e.g., moveable walls 112, 412, 512, 612, 712) to change a volume of the flow channel. The moving of the one or more moveable walls can be by any suitable mechanism, such as by using one or more deflectors (e.g., one or more deflectors 114, 414) and a coupled motion producer 123 or via gas pressure to produce transverse movement of the one or more moveable walls (e.g., moveable walls 112, 412, 512, 612, 712, 912) from a first position to a second position that is different from the first position.

For example, the first position may be an extended position, wherein the one or more moveable walls are partially or fully extended to reduce the volume in the flow channel (e.g., flow channel 102, 402, 502, 602, 702). In the second position, the one or more moveable walls can be in a retracted orientation, such as shown in FIGS. 1B, 4A, 5, and 6, for example. Thus, the moving of the one or more moveable walls (e.g., moveable walls 112, 412, 512, 612, 712) can comprise moving the one or more moveable walls from a first position wherein the flow channel (e.g., flow channel 102, 402, 502, 602, 702, 902) has a first volume to a second position wherein the flow channel (e.g., flow channel 102, 402, 502, 602, 702, 902) has a second volume, wherein the second volume is greater than the first volume. For example, the first volume may be from 25 μl to 50 μl and the second volume can be from 50 μl to 100 μl. As discussed above, the one or more moveable walls can be moved to an intermediate position to accommodate intermediate volumes.

According to the method 1000, in 1006, test liquid 104 is received in the flow channel (e.g., flow channel 102, 402, 502, 602, 702) and the test is run, preferably with the test liquid 104 stationary in the flow channel. Following testing, the test liquid 104 is removed and a wash solution can be introduced to wash the flow channel and minimize traces of the test liquid 104 therein. The moving of the one or more moveable walls (e.g., moveable walls 112, 412, 512, 612, 712) can be before or after the test liquid 104 is received in the flow channel (e.g., flow channel 102, 402, 502, 602, 702).

Following the test and washing operations, another test of another test liquid 104, such as from another patient specimen can be conducted. Many tests can be conducted, such as 40 or more tests of different test liquids 104 before the sensor assembly 100, 200, 300, 400, 500, 600, 700 is replaced with a new sensor assembly.

As discussed above, the sequence of moving in 1004 and receiving in 1006 can be in any order. For example, the one or more moveable walls 102 may be moved/displaced in 1004 to the first (extended position or an intermediate position first, and then the test liquid 102 can be received into the flow channel (e.g., flow channel 102, 402, 502, 602, 702) in 1006.

Optionally, the one or more moveable walls 102 may be provided in a second (retracted) position first, and then the test liquid 102 can be received in 1006 into the flow channel (e.g., flow channel 102, 402, 502, 602, 702) followed by moving in 1004 the one or more moveable walls (e.g., moveable walls 112, 412, 512, 612, 712) to the first position or an intermediate position. Thus, receiving the test liquid 104 in the flow channel (e.g., flow channel 102, 402, 502, 602, 702) fills the flow channel to a first extent along the length L thereof, followed by moving in 1004 the one or more moveable walls (e.g., moveable walls 112, 412, 512, 612, 712) to move the test liquid 104 in the flow channel (e.g., flow channel 102, 402, 502, 602, 702) to a second extent along the length L, that is greater than the first extent.

Thus, it should be recognized that the moving 1004 of the one or more moveable walls (e.g., moveable walls 112, 412, 512, 612, 712) can comprise moving in 1004 the one or more moveable walls to and from a first position, to and from a second position, and possibly to and from at least one intermediate position in between the first position and the second position.

In some embodiments, a calibrator liquid can be received in the flow channel (e.g., flow channel 102, 402, 502, 602, 702) when the one or more moveable walls (e.g., moveable walls 112, 412, 512, 612, 712) are in the second position (e.g., a retracted position) or in an intermediate position in between a first (extended) position and the second (retracted) position. Moreover, it is then apparent that the flow channel contains a first volume at the first position, a second volume at the second position greater than the first volume, and an intermediate volume at the intermediate position wherein the intermediate volume is in between the first volume and the second volume.

Furthermore, the first position thus can comprise a micro-mode wherein the flow channel can contain a bio-liquid from a neonatal patient; the second position can comprises a wash-mode wherein the flow channel can contain a wash solution, and the intermediate position can comprise a normal-mode wherein the flow channel can contains a bio-liquid from an adult patient.

Additional Embodiments

In one or more additional apparatus embodiments, some of the one or more sensor elements 110 are provided in between channel side openings 106 formed in a first fixed member 108, and other ones of the one or more sensor elements 110 are provided on a second fixed member 109 across from the one or more moveable walls 112.

Moreover, the one or more moveable walls 112 can comprise one or more flexible membranes and one or more deflectors 114 are configured to contact and flex the one or more flexible membranes.

Further, the one or more moveable walls 112 can comprise one or more flexible membranes and gas pressure can be applied to flex the one or more flexible membranes.

In additional method embodiments, the moving 1004 of the one or more moveable walls 112 in the method 1000 can comprise moving 1004 from a first position to a second position.

Furthermore, the moving 1004 of the one or more moveable walls 112 in the method 1000 can comprise moving the one or more moveable walls from a first position wherein the flow channel has a first volume to a second position wherein the flow channel has a second volume that is greater than the first volume.

Furthermore, according to the method 1000, the test liquid 104 can be received in the flow channel when the one or more moveable walls are in the first position.

Further yet, according to the method 1000, a wash liquid can be received in the flow channel when the one or more moveable walls are in the second position.

Further, according to the method 1000, a calibrator liquid can be received in the flow channel when the one or more moveable walls are in the second position or in an intermediate position between the first position and the second position.

According to the method 1000, the moving 1004 of the one or more moveable walls 112 can comprise moving the one or more moveable walls to and from a first position, to and from a second position, and to and from at least one intermediate position in between the first position and the second position.

According to the method 1000, in some embodiments, the flow channel contains a first volume at the first position, the flow channel contains a second volume at the second position greater than the first volume, and the flow channel contains an intermediate volume at the intermediate position wherein the intermediate volume is in between the first volume and the second volume.

According to the method 1000, in some embodiments, the first position can comprise a micro-mode wherein the flow channel contains a bio-liquid from a neonatal patient; the second position can comprise a wash-mode wherein the flow channel contains a wash solution, and the intermediate position can comprise a normal-mode wherein the flow channel contains a bio-liquid from an adult patient.

According to the method 1000, in some embodiments, the test liquid 104 can be received in the flow channel 102 to a first extent, and then moving the one or more moveable walls 112 moves the test liquid 104 in the flow channel 102 to a second extent, different than the first extent.

While embodiments of this disclosure have been disclosed in example forms, many modifications, additions, and deletions can be made therein without departing from the scope of this disclosure, as set forth in the claims and their equivalents.

What is claimed is:

1. A sensor assembly, comprising:

a gas pressure source;

a sensor body having a flow channel configured to receive a test liquid therein, one or more moveable walls that continuously define at least one sidewall of the flow channel along a length of the flow channel, the one or more moveable walls configured to be moveable via pressurized gas provided by the gas pressure source to displace the sidewall itself and change a volume of the flow channel; and one or more sensor elements positioned in the flow channel.

2. The sensor assembly of claim 1, wherein the one or more sensor elements are positioned at one or more locations where the one or more sensor elements can be contacted by the test liquid.

3. The sensor assembly of claim 1, wherein the one or more sensor elements comprise one or more analyte sensor elements.

4. The sensor assembly of claim 1, wherein the one or more sensor elements comprise an array of analyte sensor elements arranged along a length of the flow channel.

5. The sensor assembly of claim 1, wherein the one or more sensor elements are configured to test for a concentration of a constituent contained in the test liquid.

6. The sensor assembly of claim 1, wherein the test liquid is a liquid selected from a group comprising:

whole blood, blood serum or plasma, urine, cerebrospinal fluid, dialysate, serous fluid, interstitial fluid, synovial fluid, intraocular fluid, lymph plasma, digestive fluid, and human tissue-containing liquid.

7. The sensor assembly of claim 1, wherein the one or more moveable walls are configured to be moveable from a first position to a second position.

8. The sensor assembly of claim 1, wherein the one or more moveable walls are configured to be moveable from an un-extended orientation to an extended orientation.

9. The sensor assembly of claim 1, wherein the flow channel is formed, in part, by a first fixed member having one or more channel side openings formed therein.

10. The sensor assembly of claim 1, wherein the one or more moveable walls comprise one or more flexible membranes.

11. The sensor assembly of claim 10, wherein the one or more flexible membranes are configured to flex from one or more channel side openings.

12. The sensor assembly of claim 10, wherein the one or more flexible membranes comprise a flexible polymer.

13. The sensor assembly of claim 12, wherein the flexible polymer comprises polyethylene perephthalate (PET), polyvinylpyrrolidone (PVP), thermoplastic elastomer (TPE), or ethylene propylene diene terpolymer (EPDM).

14. The sensor assembly of claim 1, wherein the one or more moveable walls are operably moveable to constrict a transverse cross-sectional area of the flow channel.

15. The sensor assembly of claim 1, wherein the one or more moveable walls are formed from one or more flexible membranes that are bonded to a first fixed member comprising one or more channel side openings.

16. The sensor assembly of claim 1, wherein the one or more moveable walls comprises a single moveable wall extending along 50% or more of a length of the flow channel.

17. The sensor assembly of claim 1, wherein the one or more moveable walls comprises a membrane bonded to a first fixed member and forming a side of the flow channel.

18. The sensor assembly of claim 1, wherein at least some of the one or more sensor elements are provided on the one or more moveable walls.

* * * * *